(12) United States Patent
Bellas et al.

(10) Patent No.: US 10,206,784 B2
(45) Date of Patent: Feb. 19, 2019

(54) POSTERIOR INTERVERTEBRAL DISC INSERTER AND EXPANSION TECHNIQUES

(71) Applicant: DePuy Synthes Products, Inc., Raynham, MA (US)

(72) Inventors: Jonathan Bellas, East Taunton, MA (US); Seung-kyu Daniel Kwak, Wayne, PA (US); Michael J. O'Neil, West Barnstable, MA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/611,890

(22) Filed: Jun. 2, 2017

(65) Prior Publication Data

US 2017/0304068 A1     Oct. 26, 2017

Related U.S. Application Data

(63) Continuation of application No. 14/922,360, filed on Oct. 26, 2015, now Pat. No. 9,687,354, which is a (Continued)

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4611* (2013.01); *A61F 2/4425* (2013.01); *A61F 2002/3052* (2013.01); *A61F 2002/30116* (2013.01); *A61F 2002/30179* (2013.01); *A61F 2002/30181* (2013.01); *A61F 2002/30405* (2013.01); *A61F 2002/30471* (2013.01); *A61F 2002/30579* (2013.01); *A61F 2002/30617* (2013.01); *A61F 2002/4415* (2013.01); *A61F 2002/4627* (2013.01); *A61F 2220/0025* (2013.01); *A61F 2220/0091* (2013.01); *A61F 2230/0006* (2013.01); *A61F 2230/006* (2013.01); *A61F 2230/0058* (2013.01); *A61F 2250/0097* (2013.01)

(58) Field of Classification Search
CPC ..................... A61F 2/44–2/447; A61F 2/4611
See application file for complete search history.

(56) References Cited

U.S. PATENT DOCUMENTS

| | | |
|---|---|---|
| 1,636,636 A | 7/1927 | Humble |
| 1,677,337 A | 7/1928 | Grove |

(Continued)

FOREIGN PATENT DOCUMENTS

| | | |
|---|---|---|
| CN | 201244104 Y | 5/2009 |
| DE | 19710392 C1 | 7/1999 |

(Continued)

OTHER PUBLICATIONS

Vandorpe et al in the Handbook of Biodegradable Polymers, edited by Domb et al., Hardwood Academic Press, p. 161-182, 1997.

(Continued)

*Primary Examiner* — Eduardo C Robert
*Assistant Examiner* — Michelle C Eckman
(74) *Attorney, Agent, or Firm* — Baker & Hostetler LLP

(57) ABSTRACT

Insertion and expansion devices for use in inserting motion discs, and associated methods of use.

20 Claims, 7 Drawing Sheets

Related U.S. Application Data continuation of application No. 12/055,779, filed on Mar. 26, 2008.

(56) References Cited

U.S. PATENT DOCUMENTS

| | | | |
|---|---|---|---|
| 2,304,703 | A | 12/1942 | O'Leary |
| 4,105,034 | A | 8/1978 | Shalaby et al. |
| 4,130,639 | A | 12/1978 | Shalaby et al. |
| 4,140,678 | A | 2/1979 | Shalaby et al. |
| 4,141,087 | A | 2/1979 | Shalaby et al. |
| 4,205,399 | A | 6/1980 | Jamiolkowski et al. |
| 4,208,511 | A | 6/1980 | Jamiolkowski et al. |
| 4,743,256 | A | 5/1988 | Brantigan |
| 4,904,261 | A | 2/1990 | Dove et al. |
| 4,955,908 | A | 9/1990 | Frey et al. |
| 5,041,113 | A | 8/1991 | Biedermann et al. |
| 5,123,926 | A | 6/1992 | Pisharodi |
| 5,147,361 | A | 9/1992 | Ojima et al. |
| 5,209,751 | A | 5/1993 | Farris et al. |
| 5,306,308 | A | 4/1994 | Gross et al. |
| 5,352,231 | A | 10/1994 | Brumfield et al. |
| 5,391,170 | A | 2/1995 | McGuire et al. |
| 5,395,372 | A | 3/1995 | Holt et al. |
| 5,397,364 | A | 3/1995 | Kozak et al. |
| 5,443,514 | A | 8/1995 | Steffee |
| 5,443,515 | A | 8/1995 | Cohen et al. |
| 5,464,407 | A | 11/1995 | McGuire |
| 5,464,929 | A | 11/1995 | Bezwada et al. |
| 5,499,986 | A | 3/1996 | Dimarco |
| 5,529,580 | A | 6/1996 | Kusunoki et al. |
| 5,534,031 | A | 7/1996 | Matsuzaki et al. |
| 5,578,034 | A | 11/1996 | Estes |
| 5,591,166 | A | 1/1997 | Bernhardt et al. |
| 5,595,751 | A | 1/1997 | Bezwada et al. |
| 5,597,579 | A | 1/1997 | Bezwada et al. |
| 5,601,553 | A | 2/1997 | Trebing et al. |
| 5,607,687 | A | 3/1997 | Bezwada et al. |
| 5,609,636 | A | 3/1997 | Kohrs et al. |
| 5,618,552 | A | 4/1997 | Bezwada et al. |
| 5,620,458 | A | 4/1997 | Green et al. |
| 5,620,698 | A | 4/1997 | Bezwada et al. |
| 5,645,598 | A | 7/1997 | Brosnahan, III |
| 5,645,850 | A | 7/1997 | Bezwada et al. |
| 5,648,088 | A | 7/1997 | Bezwada et al. |
| 5,662,655 | A | 9/1997 | Laboureau et al. |
| 5,676,666 | A | 10/1997 | Oxland et al. |
| 5,698,213 | A | 12/1997 | Jamiolkowski et al. |
| 5,700,583 | A | 12/1997 | Jamiolkowski et al. |
| 5,713,899 | A | 2/1998 | Marnay et al. |
| 5,716,415 | A | 2/1998 | Steffee |
| 5,755,796 | A | 5/1998 | Ibo et al. |
| 5,776,196 | A | 7/1998 | Matsuzaki et al. |
| 5,779,707 | A | 7/1998 | Bertholet et al. |
| 5,785,713 | A | 7/1998 | Jobe |
| 5,788,698 | A | 8/1998 | Savornin |
| 5,797,912 | A | 8/1998 | Runciman et al. |
| 5,797,918 | A | 8/1998 | McGuire et al. |
| 5,800,435 | A | 9/1998 | Errico et al. |
| 5,800,440 | A | 9/1998 | Stead |
| 5,859,150 | A | 1/1999 | Jamiolkowski et al. |
| 5,888,223 | A | 3/1999 | Bray, Jr. |
| 5,904,689 | A | 5/1999 | Jonjic |
| 5,913,860 | A | 6/1999 | Scholl |
| 6,039,761 | A | 3/2000 | Li et al. |
| 6,049,026 | A | 4/2000 | Muschler |
| 6,056,749 | A | 5/2000 | Kuslich |
| 6,066,175 | A | 5/2000 | Henderson et al. |
| 6,086,593 | A | 7/2000 | Bonutti |
| 6,093,205 | A | 7/2000 | McLeod et al. |
| 6,099,531 | A | 8/2000 | Bonutti |
| 6,106,557 | A | 8/2000 | Robioneck et al. |
| 6,117,174 | A | 9/2000 | Nolan |
| 6,120,503 | A | 9/2000 | Michelson |
| 6,126,689 | A | 10/2000 | Brett |
| 6,139,550 | A | 10/2000 | Michelson |
| 6,156,037 | A | 12/2000 | Lehuec et al. |
| 6,159,211 | A | 12/2000 | Boriani et al. |
| 6,159,244 | A | 12/2000 | Suddaby |
| 6,174,311 | B1 | 1/2001 | Branch et al. |
| 6,179,875 | B1 | 1/2001 | Von Strempel |
| 6,190,414 | B1 | 2/2001 | Young et al. |
| 6,193,757 | B1 * | 2/2001 | Foley .............. A61F 2/4455 623/17.16 |
| 6,200,306 | B1 | 3/2001 | Klostermeyer et al. |
| 6,206,922 | B1 | 3/2001 | Zdeblick et al. |
| 6,224,602 | B1 | 5/2001 | Hayes |
| 6,231,610 | B1 | 5/2001 | Geisler |
| 6,235,059 | B1 | 5/2001 | Benezech et al. |
| 6,306,170 | B2 | 10/2001 | Ray |
| 6,330,845 | B1 | 12/2001 | Meulink |
| 6,336,928 | B1 | 1/2002 | Guerin et al. |
| 6,342,055 | B1 | 1/2002 | Eisermann et al. |
| 6,342,074 | B1 | 1/2002 | Simpson |
| 6,364,880 | B1 | 4/2002 | Michelson |
| 6,368,351 | B1 | 4/2002 | Glenn et al. |
| 6,375,462 | B1 | 4/2002 | Holweg et al. |
| 6,387,130 | B1 | 5/2002 | Stone et al. |
| 6,395,031 | B1 | 5/2002 | Foley et al. |
| 6,406,478 | B1 | 6/2002 | Kuo |
| 6,409,766 | B1 | 6/2002 | Brett |
| 6,413,278 | B1 | 7/2002 | Marchosky |
| 6,423,063 | B1 | 7/2002 | Bonutti |
| 6,428,575 | B2 | 8/2002 | Koo et al. |
| 6,432,106 | B1 | 8/2002 | Fraser |
| 6,447,544 | B1 | 9/2002 | Michelson |
| 6,447,546 | B1 | 9/2002 | Bramlet et al. |
| 6,454,769 | B2 | 9/2002 | Wagner et al. |
| 6,461,359 | B1 | 10/2002 | Tribus et al. |
| 6,471,724 | B2 | 10/2002 | Zdeblick et al. |
| 6,488,710 | B2 | 12/2002 | Besselink |
| 6,508,818 | B2 | 1/2003 | Steiner et al. |
| 6,558,387 | B2 | 5/2003 | Errico et al. |
| 6,558,423 | B1 | 5/2003 | Michelson |
| 6,562,073 | B2 | 5/2003 | Foley |
| 6,565,570 | B2 | 5/2003 | Sterett et al. |
| 6,572,619 | B2 | 6/2003 | Santilli |
| 6,579,290 | B1 | 6/2003 | Hardcastle et al. |
| 6,602,257 | B1 | 8/2003 | Thramann |
| 6,629,998 | B1 | 10/2003 | Lin |
| 6,682,563 | B2 | 1/2004 | Scharf |
| 6,695,846 | B2 | 2/2004 | Richelsoph et al. |
| 6,730,125 | B1 | 5/2004 | Lin |
| 6,730,127 | B2 | 5/2004 | Michelson |
| 6,733,531 | B1 | 5/2004 | Trieu |
| 6,736,850 | B2 | 5/2004 | Davis |
| 6,743,257 | B2 | 6/2004 | Castro |
| 6,745,255 | B2 | 6/2004 | Yen et al. |
| 6,761,738 | B1 | 7/2004 | Boyd |
| 6,770,096 | B2 | 8/2004 | Bolger et al. |
| 6,773,437 | B2 | 8/2004 | Ogilvie et al. |
| 6,776,781 | B1 | 8/2004 | Uwaydah |
| 6,805,714 | B2 | 10/2004 | Sutcliffe |
| 6,808,537 | B2 | 10/2004 | Michelson |
| 6,824,564 | B2 | 11/2004 | Crozet |
| 6,824,565 | B2 | 11/2004 | Muhanna et al. |
| 6,833,006 | B2 | 12/2004 | Foley et al. |
| 6,835,208 | B2 | 12/2004 | Marchosky |
| 6,837,905 | B1 | 1/2005 | Lieberman |
| 6,849,093 | B2 | 2/2005 | Michelson |
| 6,890,335 | B2 | 5/2005 | Grabowski et al. |
| 6,890,355 | B2 | 5/2005 | Michelson |
| 6,945,973 | B2 | 9/2005 | Bray |
| 6,972,019 | B2 | 12/2005 | Michelson |
| 6,974,479 | B2 | 12/2005 | Trieu |
| 6,974,480 | B2 | 12/2005 | Messerli et al. |
| 6,984,234 | B2 | 1/2006 | Bray |
| 7,001,385 | B2 | 2/2006 | Bonutti |
| 7,033,394 | B2 | 4/2006 | Michelson |
| 7,041,135 | B2 | 5/2006 | Michelson |
| 7,044,971 | B2 | 5/2006 | Suddaby |
| 7,056,341 | B2 | 6/2006 | Crozet |
| 7,063,491 | B2 | 6/2006 | French |
| 7,070,598 | B2 | 7/2006 | Lim et al. |
| 7,077,864 | B2 | 7/2006 | Byrd et al. |

(56) References Cited

U.S. PATENT DOCUMENTS

| | | |
|---|---|---|
| 7,087,055 B2 | 8/2006 | Lim et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,163,561 B2 | 1/2007 | Michelson |
| 7,172,627 B2 | 2/2007 | Fiere et al. |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,238,206 B2 | 7/2007 | Lange et al. |
| 7,255,698 B2 | 8/2007 | Michelson |
| 7,276,081 B1 | 10/2007 | Coates et al. |
| 7,288,094 B2 | 10/2007 | Lindemann et al. |
| 7,288,095 B2 | 10/2007 | Baynham et al. |
| 7,288,114 B2 | 10/2007 | Lange |
| 7,306,605 B2 | 12/2007 | Ross |
| 7,309,358 B2 | 12/2007 | Berry et al. |
| 7,311,734 B2 | 12/2007 | Van et al. |
| 7,316,714 B2 | 1/2008 | Gordon et al. |
| 7,318,839 B2 | 1/2008 | Malberg et al. |
| 7,323,011 B2 | 1/2008 | Shepard et al. |
| 7,326,248 B2 | 2/2008 | Michelson |
| 7,332,209 B2 | 2/2008 | Yokouchi et al. |
| 7,338,525 B2 | 3/2008 | Ferree |
| 7,341,587 B2 | 3/2008 | Molz et al. |
| 7,341,590 B2 | 3/2008 | Ferree |
| 7,354,452 B2 | 4/2008 | Foley |
| 7,361,193 B2 | 4/2008 | Frey et al. |
| 7,435,262 B2 | 10/2008 | Michelson |
| 7,438,715 B2 | 10/2008 | Doubler et al. |
| 7,452,370 B2 | 11/2008 | Anderson |
| 7,491,237 B2 | 2/2009 | Randall et al. |
| 7,527,641 B2 | 5/2009 | Suh |
| 7,594,931 B2 | 9/2009 | Louis et al. |
| 7,594,932 B2 | 9/2009 | Aferzon et al. |
| 7,601,171 B2 | 10/2009 | Ainsworth et al. |
| 7,601,173 B2 | 10/2009 | Messerli et al. |
| 7,608,062 B2 | 10/2009 | Sweeney |
| 7,618,456 B2 | 11/2009 | Mathieu et al. |
| 7,628,816 B2 | 12/2009 | Magerl et al. |
| 7,641,665 B2 | 1/2010 | Zubok et al. |
| 7,655,042 B2 | 2/2010 | Foley et al. |
| 7,658,766 B2 | 2/2010 | Melkent et al. |
| 7,662,182 B2 | 2/2010 | Zubok et al. |
| 7,674,279 B2 | 3/2010 | Johnson |
| 7,704,255 B2 | 4/2010 | Michelson |
| 7,726,002 B2 | 6/2010 | Shimp et al. |
| 7,794,502 B2 | 9/2010 | Michelson |
| 7,815,643 B2 | 10/2010 | Johnson et al. |
| 7,815,681 B2 | 10/2010 | Ferguson |
| 7,846,206 B2 | 12/2010 | Oglaza et al. |
| 7,846,210 B2 | 12/2010 | Perez-Cruet et al. |
| 7,862,616 B2 | 1/2011 | Lechmann et al. |
| 7,871,441 B2 | 1/2011 | Eckman |
| 7,875,062 B2 | 1/2011 | Lindemann et al. |
| 7,875,076 B2 | 1/2011 | Mathieu et al. |
| 7,883,531 B2 | 2/2011 | De Coninck |
| 7,887,591 B2 | 2/2011 | Aebi et al. |
| 7,887,595 B1 | 2/2011 | Pimenta |
| 7,909,877 B2 | 3/2011 | Krueger et al. |
| 7,993,403 B2 | 8/2011 | Foley et al. |
| 8,002,808 B2 | 8/2011 | Morrison et al. |
| 8,007,523 B2 | 8/2011 | Wagner et al. |
| 8,187,329 B2 | 5/2012 | Theofilos |
| 8,206,423 B2 | 6/2012 | Siegal |
| 8,216,312 B2 | 7/2012 | Gray |
| 8,236,029 B2 | 8/2012 | Siegal |
| 8,241,328 B2 | 8/2012 | Siegal |
| 8,246,622 B2 | 8/2012 | Siegal et al. |
| 8,323,342 B2 | 12/2012 | Schwab |
| 8,328,812 B2 | 12/2012 | Siegal et al. |
| 8,337,559 B2 | 12/2012 | Hansell et al. |
| 8,343,219 B2 | 1/2013 | Allain et al. |
| 8,349,015 B2 | 1/2013 | Bae et al. |
| 8,357,200 B2 | 1/2013 | Adl |
| 8,454,694 B2 | 6/2013 | Armstrong et al. |
| 8,460,385 B1 | 6/2013 | Wensel |
| 8,460,387 B2 | 6/2013 | Theofilos |
| 8,465,524 B2 | 6/2013 | Siegal |
| 8,470,044 B2 | 6/2013 | Bertholet et al. |
| 8,480,747 B2 | 7/2013 | Melkent et al. |
| 8,486,109 B2 | 7/2013 | Siegal |
| 8,491,658 B1 | 7/2013 | Etminan |
| 8,496,691 B2 | 7/2013 | Blain |
| 8,496,708 B2 | 7/2013 | Blain |
| 8,500,783 B2 | 8/2013 | Baynham |
| 8,551,175 B1 | 10/2013 | Wensel |
| 8,562,651 B2 | 10/2013 | Metcalf et al. |
| 8,597,330 B2 | 12/2013 | Siegal |
| 8,613,772 B2 | 12/2013 | Bray et al. |
| 8,617,245 B2 | 12/2013 | Brett |
| 8,628,578 B2 | 1/2014 | Miller et al. |
| 8,641,765 B2 | 2/2014 | Muhanna |
| 8,672,977 B2 | 3/2014 | Siegal et al. |
| 8,690,928 B1 | 4/2014 | Walkenhorst et al. |
| 8,690,948 B2 | 4/2014 | Armstrong et al. |
| 8,747,443 B2 | 6/2014 | Aferzon |
| 8,758,439 B2 | 6/2014 | Linares |
| 8,777,993 B2 | 7/2014 | Siegal et al. |
| 8,821,555 B2 | 9/2014 | Bae et al. |
| 8,845,638 B2 | 9/2014 | Siegal et al. |
| 8,900,235 B2 | 12/2014 | Siegal |
| 8,906,098 B2 | 12/2014 | Siegal |
| 8,932,359 B2 | 1/2015 | Brett |
| 8,956,416 B2 | 2/2015 | McCarthy |
| 9,005,293 B2 | 4/2015 | Moskowitz et al. |
| 9,005,295 B2 | 4/2015 | Kueenzi et al. |
| 9,017,408 B2 | 4/2015 | Siegal et al. |
| 9,017,413 B2 | 4/2015 | Siegal et al. |
| 9,044,334 B2 | 6/2015 | Siegal et al. |
| 9,138,330 B2 | 9/2015 | Hansell et al. |
| 9,192,419 B2 | 11/2015 | McDonough et al. |
| 9,248,028 B2 | 2/2016 | Gamache |
| 9,254,138 B2 | 2/2016 | Siegal et al. |
| 9,265,546 B2 | 2/2016 | Blain |
| 9,265,621 B2 | 2/2016 | Voellmicke |
| 9,271,836 B2 | 3/2016 | Pavento et al. |
| 9,278,009 B2 | 3/2016 | Bray et al. |
| 9,283,091 B2 | 3/2016 | Melkent et al. |
| 9,283,092 B2 | 3/2016 | Siegal et al. |
| 9,289,311 B1 | 3/2016 | Whipple |
| 9,364,272 B2 | 6/2016 | Binder et al. |
| 9,402,735 B2 | 8/2016 | McDonough et al. |
| 9,402,738 B2 | 8/2016 | Niemiec et al. |
| 9,408,712 B2 | 8/2016 | Siegal et al. |
| 9,492,286 B2 | 11/2016 | Biedermann et al. |
| 9,662,225 B2 | 5/2017 | Pavento et al. |
| 9,668,877 B2 | 6/2017 | Pavento et al. |
| 2001/0031968 A1 | 10/2001 | Dorchak et al. |
| 2002/0029044 A1 | 3/2002 | Monassevitch et al. |
| 2002/0029082 A1 | 3/2002 | Muhanna |
| 2002/0095155 A1 | 7/2002 | Michelson |
| 2002/0099376 A1 | 7/2002 | Michelson |
| 2002/0138146 A1 | 9/2002 | Jackson |
| 2002/0143328 A1 | 10/2002 | Shluzas et al. |
| 2002/0151976 A1 | 10/2002 | Foley et al. |
| 2002/0156475 A1 | 10/2002 | Lerch et al. |
| 2003/0004576 A1 | 1/2003 | Thalgott |
| 2003/0023305 A1 | 1/2003 | McKay |
| 2003/0028197 A1 | 2/2003 | Hanson et al. |
| 2003/0045940 A1 | 3/2003 | Eberlein et al. |
| 2003/0050645 A1 | 3/2003 | Parker et al. |
| 2003/0083748 A1 | 5/2003 | Lee et al. |
| 2003/0100949 A1 | 5/2003 | Michelson |
| 2003/0125739 A1 | 7/2003 | Bagga et al. |
| 2003/0130739 A1 | 7/2003 | Gerbec et al. |
| 2003/0153975 A1 | 8/2003 | Byrd et al. |
| 2003/0158555 A1 | 8/2003 | Sanders et al. |
| 2003/0187440 A1 | 10/2003 | Richelsoph et al. |
| 2003/0187506 A1 | 10/2003 | Ross et al. |
| 2003/0195632 A1 | 10/2003 | Foley et al. |
| 2003/0225409 A1 | 12/2003 | Freid et al. |

(56) References Cited

U.S. PATENT DOCUMENTS

| | | |
|---|---|---|
| 2004/0024464 A1 | 2/2004 | Errico et al. |
| 2004/0034430 A1 | 2/2004 | Falahee |
| 2004/0092929 A1 | 5/2004 | Zindrick |
| 2004/0106996 A1 | 6/2004 | Liu et al. |
| 2004/0111089 A1 | 6/2004 | Stevens et al. |
| 2004/0127902 A1 | 7/2004 | Suzuki et al. |
| 2004/0127990 A1 | 7/2004 | Bartish et al. |
| 2004/0138662 A1 | 7/2004 | Landry et al. |
| 2004/0153065 A1 | 8/2004 | Lim |
| 2004/0153072 A1 | 8/2004 | Bonutti |
| 2004/0167625 A1 | 8/2004 | Beyar et al. |
| 2004/0193269 A1 | 9/2004 | Fraser et al. |
| 2004/0199253 A1 | 10/2004 | Link et al. |
| 2004/0199254 A1 | 10/2004 | Louis et al. |
| 2004/0210219 A1 | 10/2004 | Bray |
| 2004/0249377 A1 | 12/2004 | Kaes et al. |
| 2004/0254644 A1 | 12/2004 | Taylor |
| 2004/0260286 A1 | 12/2004 | Ferree |
| 2005/0021144 A1 | 1/2005 | Malberg et al. |
| 2005/0033433 A1 | 2/2005 | Michelson |
| 2005/0038513 A1 | 2/2005 | Michelson |
| 2005/0043800 A1* | 2/2005 | Paul .............. A61B 17/1671 623/17.15 |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser et al. |
| 2005/0096657 A1 | 5/2005 | Autericque et al. |
| 2005/0101960 A1 | 5/2005 | Fiere et al. |
| 2005/0113920 A1 | 5/2005 | Foley et al. |
| 2005/0143749 A1 | 6/2005 | Zalenski et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0177240 A1 | 8/2005 | Blain |
| 2005/0177245 A1 | 8/2005 | Leatherbury et al. |
| 2005/0182416 A1 | 8/2005 | Lim et al. |
| 2005/0209696 A1 | 9/2005 | Lin et al. |
| 2005/0251260 A1 | 11/2005 | Gerber et al. |
| 2005/0261768 A1 | 11/2005 | Trieu |
| 2005/0277938 A1 | 12/2005 | Parsons |
| 2005/0278036 A1 | 12/2005 | Leonard et al. |
| 2006/0025860 A1 | 2/2006 | Li |
| 2006/0030851 A1 | 2/2006 | Bray et al. |
| 2006/0058801 A1 | 3/2006 | Schlienger et al. |
| 2006/0079961 A1 | 4/2006 | Michelson |
| 2006/0085071 A1 | 4/2006 | Lechmann et al. |
| 2006/0129424 A1 | 6/2006 | Chan |
| 2006/0142765 A9 | 6/2006 | Dixon et al. |
| 2006/0142858 A1 | 6/2006 | Colleran et al. |
| 2006/0142863 A1 | 6/2006 | Fraser |
| 2006/0178745 A1 | 8/2006 | Bartish et al. |
| 2006/0211952 A1 | 9/2006 | Kennedy, II |
| 2006/0229609 A1 | 10/2006 | Wang |
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235518 A1 | 10/2006 | Blain |
| 2006/0235535 A1 | 10/2006 | Ferree et al. |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0259147 A1 | 11/2006 | Krishna et al. |
| 2006/0265068 A1* | 11/2006 | Schwab .............. A61B 17/7067 623/17.11 |
| 2006/0293753 A1 | 12/2006 | Thramann |
| 2007/0049941 A1 | 3/2007 | Thramann |
| 2007/0055252 A1 | 3/2007 | Blain et al. |
| 2007/0067035 A1 | 3/2007 | Falahee |
| 2007/0073398 A1* | 3/2007 | Fabian ............... A61F 2/442 623/17.11 |
| 2007/0106384 A1 | 5/2007 | Bray et al. |
| 2007/0106388 A1 | 5/2007 | Michelson |
| 2007/0129804 A1 | 6/2007 | Bentley et al. |
| 2007/0162138 A1 | 7/2007 | Heinz |
| 2007/0198016 A1 | 8/2007 | Zang et al. |
| 2007/0213737 A1 | 9/2007 | Schermerhorn et al. |
| 2007/0213820 A1 | 9/2007 | Magerl et al. |
| 2007/0219635 A1 | 9/2007 | Mathieu et al. |
| 2007/0233118 A1 | 10/2007 | McLain |
| 2007/0233253 A1 | 10/2007 | Bray et al. |
| 2007/0233261 A1 | 10/2007 | Lopez et al. |
| 2007/0233263 A1 | 10/2007 | Melkent et al. |
| 2007/0250167 A1 | 10/2007 | Bray et al. |
| 2007/0255416 A1 | 11/2007 | Melkent et al. |
| 2007/0265631 A1 | 11/2007 | Fox |
| 2007/0270957 A1 | 11/2007 | Heinz |
| 2007/0270965 A1 | 11/2007 | Ferguson |
| 2007/0276490 A1 | 11/2007 | Mateyka |
| 2007/0282449 A1* | 12/2007 | de Villiers ........... A61F 2/4425 623/17.15 |
| 2007/0293948 A1 | 12/2007 | Bagga et al. |
| 2007/0299521 A1* | 12/2007 | Glenn ................. A61F 2/4425 623/17.11 |
| 2008/0015694 A1 | 1/2008 | Tribus |
| 2008/0027550 A1 | 1/2008 | Link et al. |
| 2008/0033440 A1 | 2/2008 | Moskowitz et al. |
| 2008/0051890 A1 | 2/2008 | Waugh et al. |
| 2008/0051897 A1* | 2/2008 | Lopez ................. A61F 2/4611 623/17.13 |
| 2008/0065219 A1 | 3/2008 | Dye |
| 2008/0077247 A1 | 3/2008 | Murillo et al. |
| 2008/0082173 A1 | 4/2008 | Delurio et al. |
| 2008/0097436 A1 | 4/2008 | Culbert et al. |
| 2008/0103597 A1* | 5/2008 | Lechmann ........... A61F 2/4425 623/17.16 |
| 2008/0103598 A1 | 5/2008 | Trudeau et al. |
| 2008/0109005 A1 | 5/2008 | Trudeau et al. |
| 2008/0125865 A1 | 5/2008 | Abdelgany |
| 2008/0132949 A1 | 6/2008 | Aferzon et al. |
| 2008/0132958 A1 | 6/2008 | Pech et al. |
| 2008/0133012 A1 | 6/2008 | McGuckin |
| 2008/0133014 A1* | 6/2008 | Gately ................. A61F 2/4425 623/17.16 |
| 2008/0161925 A1 | 7/2008 | Brittan et al. |
| 2008/0167666 A1 | 7/2008 | Fiere et al. |
| 2008/0177307 A1 | 7/2008 | Moskowitz et al. |
| 2008/0183293 A1 | 7/2008 | Parry et al. |
| 2008/0183294 A1 | 7/2008 | Adl |
| 2008/0221690 A1 | 9/2008 | Chaput et al. |
| 2008/0221694 A1 | 9/2008 | Warnick et al. |
| 2008/0234822 A1 | 9/2008 | Govil et al. |
| 2008/0243136 A1 | 10/2008 | Prager et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0255620 A1 | 10/2008 | Strauss et al. |
| 2008/0269806 A1 | 10/2008 | Zhang et al. |
| 2008/0281425 A1 | 11/2008 | Thalgott et al. |
| 2008/0294262 A1 | 11/2008 | Levieux |
| 2008/0300601 A1* | 12/2008 | Fabian ................. A61B 17/025 606/90 |
| 2008/0300634 A1 | 12/2008 | Gray |
| 2008/0306596 A1 | 12/2008 | Jones et al. |
| 2008/0306598 A1 | 12/2008 | Hansen et al. |
| 2008/0312698 A1 | 12/2008 | Bergeron et al. |
| 2008/0312742 A1 | 12/2008 | Abernathie |
| 2009/0012529 A1 | 1/2009 | Blain et al. |
| 2009/0030421 A1 | 1/2009 | Hawkins et al. |
| 2009/0030519 A1 | 1/2009 | Falahee |
| 2009/0030520 A1 | 1/2009 | Biedermann et al. |
| 2009/0062921 A1 | 3/2009 | Michelson |
| 2009/0088849 A1 | 4/2009 | Armstrong et al. |
| 2009/0099554 A1 | 4/2009 | Forster et al. |
| 2009/0099610 A1 | 4/2009 | Johnson et al. |
| 2009/0099661 A1 | 4/2009 | Bhattacharya et al. |
| 2009/0105771 A1 | 4/2009 | Lei et al. |
| 2009/0105774 A1 | 4/2009 | Jones et al. |
| 2009/0105830 A1 | 4/2009 | Jones et al. |
| 2009/0105831 A1 | 4/2009 | Jones et al. |
| 2009/0125028 A1 | 5/2009 | Teisen et al. |

(56) References Cited

U.S. PATENT DOCUMENTS

| | | |
|---|---|---|
| 2009/0131988 A1 | 5/2009 | Bush et al. |
| 2009/0132054 A1 | 5/2009 | Zeegers |
| 2009/0143859 A1 | 6/2009 | McClellan et al. |
| 2009/0164020 A1 | 6/2009 | Janowski et al. |
| 2009/0182428 A1 | 7/2009 | McClellan et al. |
| 2009/0182430 A1 | 7/2009 | Tyber et al. |
| 2009/0192549 A1 | 7/2009 | Sanders et al. |
| 2009/0192613 A1 | 7/2009 | Wing et al. |
| 2009/0192614 A1 | 7/2009 | Beger et al. |
| 2009/0192615 A1 | 7/2009 | Tyber et al. |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott et al. |
| 2009/0210064 A1 | 8/2009 | Lechmann et al. |
| 2009/0224023 A1 | 9/2009 | Moskowitz et al. |
| 2009/0234364 A1* | 9/2009 | Crook ............... A61F 2/4465 606/99 |
| 2009/0248092 A1* | 10/2009 | Bellas ............... A61F 2/4611 606/86 A |
| 2009/0259316 A1 | 10/2009 | Ginn et al. |
| 2009/0265007 A1 | 10/2009 | Colleran |
| 2009/0270873 A1* | 10/2009 | Fabian ............... A61F 2/442 606/99 |
| 2009/0287251 A1 | 11/2009 | Bae et al. |
| 2009/0306779 A1 | 12/2009 | Ahn |
| 2009/0326543 A1* | 12/2009 | Fabian, Jr. ........... A61F 2/4611 606/99 |
| 2009/0326580 A1 | 12/2009 | Anderson et al. |
| 2009/0326589 A1 | 12/2009 | Lemoine et al. |
| 2010/0004747 A1 | 1/2010 | Lin |
| 2010/0016901 A1 | 1/2010 | Robinson |
| 2010/0016973 A1* | 1/2010 | de Villiers ........... A61F 2/4425 623/17.16 |
| 2010/0023128 A1 | 1/2010 | Malberg |
| 2010/0030334 A1 | 2/2010 | Molz, IV |
| 2010/0036496 A1 | 2/2010 | Yu et al. |
| 2010/0042159 A1 | 2/2010 | Butler |
| 2010/0057206 A1 | 3/2010 | Duffield et al. |
| 2010/0069969 A1 | 3/2010 | Ampuero et al. |
| 2010/0070037 A1 | 3/2010 | Parry et al. |
| 2010/0087925 A1 | 4/2010 | Kostuik et al. |
| 2010/0106249 A1 | 4/2010 | Tyber et al. |
| 2010/0137987 A1* | 6/2010 | Diao ............... A61B 17/7095 623/17.15 |
| 2010/0145457 A1 | 6/2010 | Felt et al. |
| 2010/0145459 A1 | 6/2010 | McDonough et al. |
| 2010/0145460 A1 | 6/2010 | McDonough et al. |
| 2010/0179656 A1 | 7/2010 | Theofilos |
| 2010/0185287 A1 | 7/2010 | Allard et al. |
| 2010/0185289 A1 | 7/2010 | Kirwan et al. |
| 2010/0185292 A1 | 7/2010 | Hochschuler et al. |
| 2010/0204739 A1 | 8/2010 | Bae et al. |
| 2010/0217325 A1 | 8/2010 | Hochschuler et al. |
| 2010/0217393 A1 | 8/2010 | Theofilos |
| 2010/0249935 A1 | 9/2010 | Slivka et al. |
| 2010/0249937 A1 | 9/2010 | Blain et al. |
| 2010/0286777 A1 | 11/2010 | Errico et al. |
| 2010/0286781 A1 | 11/2010 | Bullard |
| 2010/0286783 A1 | 11/2010 | Lechmann et al. |
| 2010/0292696 A1 | 11/2010 | Chantelot et al. |
| 2010/0292737 A1 | 11/2010 | Suh |
| 2010/0305704 A1 | 12/2010 | Messerli et al. |
| 2010/0312345 A1 | 12/2010 | Duffield et al. |
| 2010/0312346 A1 | 12/2010 | Kueenzi et al. |
| 2011/0009908 A1 | 1/2011 | Ferguson |
| 2011/0009966 A1 | 1/2011 | Michelson |
| 2011/0015675 A1 | 1/2011 | Howard et al. |
| 2011/0015745 A1 | 1/2011 | Bucci |
| 2011/0082550 A1 | 4/2011 | Yeh |
| 2011/0082555 A1 | 4/2011 | Martz et al. |
| 2011/0098747 A1 | 4/2011 | Donner et al. |
| 2011/0106159 A1 | 5/2011 | Nazeck |
| 2011/0144703 A1 | 6/2011 | Krause et al. |
| 2011/0166656 A1 | 7/2011 | Thalgott et al. |
| 2011/0184415 A1 | 7/2011 | Anderson et al. |
| 2011/0190892 A1 | 8/2011 | Kirschman |
| 2011/0202136 A1 | 8/2011 | Britian et al. |
| 2011/0208311 A1 | 8/2011 | Janowski |
| 2011/0213421 A1 | 9/2011 | Binder et al. |
| 2011/0230971 A1 | 9/2011 | Donner et al. |
| 2011/0251689 A1 | 10/2011 | Seifert et al. |
| 2011/0319998 A1 | 12/2011 | O'Neil et al. |
| 2012/0041559 A1 | 2/2012 | Melkent et al. |
| 2012/0078371 A1 | 3/2012 | Gamache et al. |
| 2012/0078372 A1 | 3/2012 | Gamache et al. |
| 2012/0078373 A1 | 3/2012 | Gamache et al. |
| 2012/0083889 A1 | 4/2012 | Purcell et al. |
| 2012/0150301 A1 | 6/2012 | Gamache et al. |
| 2012/0150303 A1 | 6/2012 | Linares |
| 2012/0158143 A1 | 6/2012 | Shapiro |
| 2012/0191190 A1 | 7/2012 | Trieu |
| 2012/0197401 A1 | 8/2012 | Duncan et al. |
| 2012/0203230 A1 | 8/2012 | Adams |
| 2012/0209331 A1 | 8/2012 | Michelson |
| 2012/0226319 A1 | 9/2012 | Armstrong et al. |
| 2012/0253406 A1 | 10/2012 | Bae et al. |
| 2013/0041471 A1* | 2/2013 | Siegal ............... A61F 2/442 623/17.16 |
| 2013/0060337 A1 | 3/2013 | Petersheim et al. |
| 2013/0073044 A1 | 3/2013 | Gamache |
| 2013/0079883 A1* | 3/2013 | Butler ............... A61F 2/4425 623/17.16 |
| 2013/0166027 A1 | 6/2013 | Bellas |
| 2013/0238095 A1 | 9/2013 | Pavento et al. |
| 2013/0268080 A1 | 10/2013 | Melkent et al. |
| 2013/0310939 A1* | 11/2013 | Fabian ............... A61F 2/442 623/17.16 |
| 2013/0325071 A1 | 12/2013 | Niemiec et al. |
| 2013/0345813 A1 | 12/2013 | Frank et al. |
| 2014/0039623 A1 | 2/2014 | Iott et al. |
| 2014/0067069 A1 | 3/2014 | Lopez |
| 2014/0107786 A1 | 4/2014 | Geisler et al. |
| 2014/0114415 A1 | 4/2014 | Tyber |
| 2014/0135930 A1 | 5/2014 | Georges |
| 2014/0142705 A1 | 5/2014 | Duffield et al. |
| 2014/0156009 A1 | 6/2014 | Armstrong et al. |
| 2014/0172103 A1 | 6/2014 | O'Neil et al. |
| 2014/0364917 A1 | 12/2014 | Sandstrom et al. |
| 2015/0297356 A1 | 10/2015 | Gamache et al. |
| 2015/0313721 A1 | 11/2015 | Gamache et al. |
| 2015/0374511 A1 | 12/2015 | Pavento et al. |
| 2016/0045325 A1 | 2/2016 | Bellas et al. |
| 2016/0128846 A1 | 5/2016 | Voellmicke |
| 2016/0213487 A1 | 7/2016 | Wilson et al. |
| 2016/0317317 A1 | 11/2016 | Marchek et al. |
| 2016/0324662 A1 | 11/2016 | McDonough et al. |
| 2017/0304068 A1* | 10/2017 | Bellas ............... A61F 2/4611 |
| 2017/0312090 A1* | 11/2017 | Sharabani ............ A61F 2/442 |

FOREIGN PATENT DOCUMENTS

| | | |
|---|---|---|
| EP | 1609444 A1 | 12/2005 |
| EP | 1683490 A2 | 7/2006 |
| EP | 1774926 A2 | 4/2007 |
| EP | 1459711 B1 | 7/2007 |
| EP | 1847240 A1 | 10/2007 |
| EP | 1506753 B1 | 9/2009 |
| FR | 2894130 A1 | 6/2007 |
| GB | 2220729 A | 1/1990 |
| GB | 2457673 A | 8/2009 |
| JP | 2006-524114 A | 10/2006 |
| JP | 2007-516808 | 6/2007 |
| JP | 2012-508044 | 4/2012 |
| WO | 98/04217 A1 | 2/1998 |
| WO | 98/34568 A1 | 8/1998 |
| WO | 99/38463 A2 | 8/1999 |
| WO | 99/52473 A1 | 10/1999 |
| WO | 01/08864 A1 | 2/2001 |
| WO | 02/13732 A2 | 2/2002 |
| WO | 03/05938 A1 | 1/2003 |
| WO | 03/05939 | 1/2003 |

(56) References Cited

FOREIGN PATENT DOCUMENTS

| WO | 2003/003951 A1 | 1/2003 |
|---|---|---|
| WO | 03/47473 A2 | 6/2003 |
| WO | 03/70128 A1 | 8/2003 |
| WO | 03/90650 A1 | 11/2003 |
| WO | 2004/069106 A1 | 8/2004 |
| WO | 2005/020861 A1 | 3/2005 |
| WO | 2006/058281 A2 | 6/2006 |
| WO | 2006/084057 A1 | 8/2006 |
| WO | 2007/003785 A1 | 1/2007 |
| WO | 2007/098288 A2 | 8/2007 |
| WO | 2007/118856 A1 | 10/2007 |
| WO | 2008/149223 A2 | 12/2008 |
| WO | 2009/025841 A1 | 2/2009 |
| WO | 2009/064644 A1 | 5/2009 |
| WO | 2009/091775 A2 | 7/2009 |
| WO | 2009/136009 A1 | 11/2009 |
| WO | 2010/028045 A1 | 3/2010 |
| WO | 2010/033786 A2 | 3/2010 |
| WO | 2010/054208 A1 | 5/2010 |
| WO | 2010/092893 A1 | 8/2010 |
| WO | 2010/099239 A2 | 9/2010 |
| WO | 2010/121028 A2 | 10/2010 |
| WO | 2011/008864 A1 | 1/2011 |
| WO | 2011/035126 A1 | 3/2011 |
| WO | 2011/080535 A1 | 7/2011 |
| WO | 2012/056119 A1 | 5/2012 |
| WO | 2013/018062 A1 | 2/2013 |
| WO | 2013/096192 A1 | 6/2013 |
| WO | 2013/191979 A1 | 12/2013 |

OTHER PUBLICATIONS

Schmiedberg, Isolation and characterization of metallic wear debris from a dynamic intervertebral disc prosthesis, J. Biomed. Mater. Res., vol. 28, Issue 11, 1277-1288, 1994.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Pederson, "Thermal Assembly of a Biomimetic Mineral/Collagen Composite", Biomaterials, 2003, vol. 2 . . . pp. 4881-4890, Elsevier,.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Kemnitzer and Kohn, in the Handbook of Biodegradable Polymers, edited by Domb, et al., Hardwood Academic Press, pp. 251-272, 1997.

Kandziora", Biomechanical Comparison of Cervical Spine Interbody Fusion Cages", Spine, vol. 26, No. 17, pp. 1850-1857, 2001, Lippincott Williams & Wilkins, Inc.

Humphries, "Anterior Fusion of the Lumbar Spine Using an Internal Fixative Device", Surgical Forum, vol. IX, p. 770-773, American College of Surgeons, 1959, Chicago, IL.

Heller, "Poly(ORTHO ESTERS)", Handbook of Biodegradable Polymers, edited by Domb, et al, Hardwood Academic Press, pp. 99-118, 1997.

Gercek, "Subsidence of Stand-Alone Cervical Cages in Anterior Interbody Fusion: Warning", Eur Spine J., vol. 12, pp. 513-516, 2003, Springer-Verlag.

Cohn, "Polymer Preprints", ACS Division of Polymer Chemistry, vol. 30(1), 1989, p. 498, (e.g. PEO/PLA).

Cohn and Younes, "Biodegradable PEO/PLA Block Copolymers", Journal of Biomaterials Research, 1988, vol. 22, pp. 993-1009.

Cain, "New Stand-Alone Anterior Lumbar Inerbody Fusion Device: Biomechanical Comparison with Established Fixation Techniques", Spine, vol. 30, No. 23, pp. 2631-2636, 2005, Lippincott Williams & Wilkins, Inc.

Allcock, "Polyphosphazenes", The Encyclopedia of Polymer Science, vol. 13, pp. 31-41, Wiley Intersciences, John Wiley & Sons, (1988).

* cited by examiner

POSTERIOR INTERVERTEBRAL DISC INSERTER AND EXPANSION TECHNIQUES

CROSS-REFERENCE TO RELATED APPLICATIONS

This is a continuation application of U.S. patent application Ser. No. 14/922,360, filed Oct. 26, 2015, which is a continuation application of U.S. patent application Ser. No. 12/055,779 filed Mar. 26, 2008, the disclosures of both of which are hereby incorporated by reference as if set forth in their entirety herein.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

There are many types of motion disc inserters disclosed in the prior art. These devices generally hold the inferior and superior endplates of the motion disc for "line of site" insertion. Positive stops and measurement devices are also employed on these inserters to determine the appropriate depth of implant placement.

PCT Published Patent Application WO 2006-058281 ("Glenn") discloses a spinal implant to be inserted between two vertebra to support and stabilize adjacent vertebra and allow for physiological motion. The invention includes an implantable device to support the vertebrae, and a minimally invasive method for inserting and deploying the device within the intervertebral space.

SUMMARY OF THE INVENTION

The present invention relates to insertion and expansion devices for use in inserting intervertebral motion discs, and associated methods of use. They are grouped into two separate devices and techniques as follows:

In a first embodiment, the inserter has a longitudinal handle having a distal pair of holders for holding a proximal end of a pivoting motion disc, wherein one of the holders is axially deployable within the handle. The pair of holders secure the proximal legs of the implant for insertion into the disc space. This assembly utilizes an implant first methodology, wherein this assembly is inserted into the disc space in an orientation wherein the implant is on the leading end of the assembly. Once the motion disc is placed into the disc space, a secondary deployer associated with the handle is activated to axially move one of the holders, thereby moving one of the legs relative to the other leg and thereby changing the disc device footprint (e.g., pivoting one of the legs). Several expansion mechanisms can be used to expand the legs of the implant.

The approach used in conjunction with this first embodiment may include one or more annular locations. For example, in some embodiments, the approach is ipsilateral. In some embodiments, the approach is contralateral, or both. In some embodiments, the first embodiment of the present invention produces an X-shaped artificial intervertebral disc in its expanded condition. However, other expanded motion disc geometries, such as an H-shape artificial intervertebral disc in its expanded condition, are also contemplated.

Therefore, in accordance with the present invention, there is provided a method of inserting a curvilinear motion disc having a first and second legs connected by a pivot, each leg having an endportion, the method comprising the steps of:
  a) providing the motion disc in a collapsed position,
  b) providing a motion disc inserter comprising a handle having a longitudinal axis and a first end having first holder and a deployer, the deployer being axially moveable along the axis of the handle,
  c) attaching the first endportion of the motion disc to the first holder,
  d) contacting the second endportion of the motion disc to the deployer,
  e) arcuately inserting the motion disc into the disc space in the collapsed condition, and
  f) axially moving the deployer to move the second leg and to expand the motion disc into an open condition.

Therefore, in accordance with the present invention, there is provided an assembly for inserting a curvilinear motion disc into a disc space, the assembly comprising:
  a) a curvilinear motion disc having first and second pivoting legs, each leg having an endportion, wherein the first and second leg endportions are in a first collapsed position, and wherein the first and second leg endportions are in a second expanded position, and
  b) an inserter comprising a handle having a longitudinal axis and a first end having a first holder and a deployer, the deployer being axially moveable along the axis of the rod, wherein the first endportion of the motion disc is attached to the first holder, and wherein the second endportion of the motion disc is attached to the deployer.

In a second embodiment, the insertion instrument possesses an insertion track. The insertion track instrument is inserted into the disc space by itself and creates an annular shield for the motion disc implant (thereby protecting the disc). It also provides a guide or track for the subsequently-placed motion disc implant insertion and placement to follow during insertion. Lastly, the guide/track facilitates expansion of the motion disc footprint by holding the central axis pivot point.

Therefore, in accordance with the present invention, there is provided a method of inserting a curvilinear motion disc having first and second endportions, the method comprising the steps of:
  a) providing the motion disc in a collapsed position wherein the first and second endportions are close together,
  b) inserting into a disc space a distal portion of a motion disc inserter comprising a tubular proximal portion and a curved distal portion comprising upper and lower rails,
  c) advancing the motion disc in the collapsed condition through the motion disc inserter to insert the motion disc into the disc space and rotate the motion disc, and
  d) expanding the motion disc into an open condition in the disc space.

The methods of the present invention differ from those of the prior art because the present methods employ non-linear insertion techniques with instruments having deployment features that expand or change the footprint of an artificial intervertebral disc implant.

Some embodiments of this invention differs from prior art because it employs an expansion means to change location and footprint of the artificial disc, wherein the expansion means is independent of the insertion method.

This invention differs from the prior art because it does not use screw attachment to couple the inserter to the implant.

DETAILED DESCRIPTION

Figure 1:
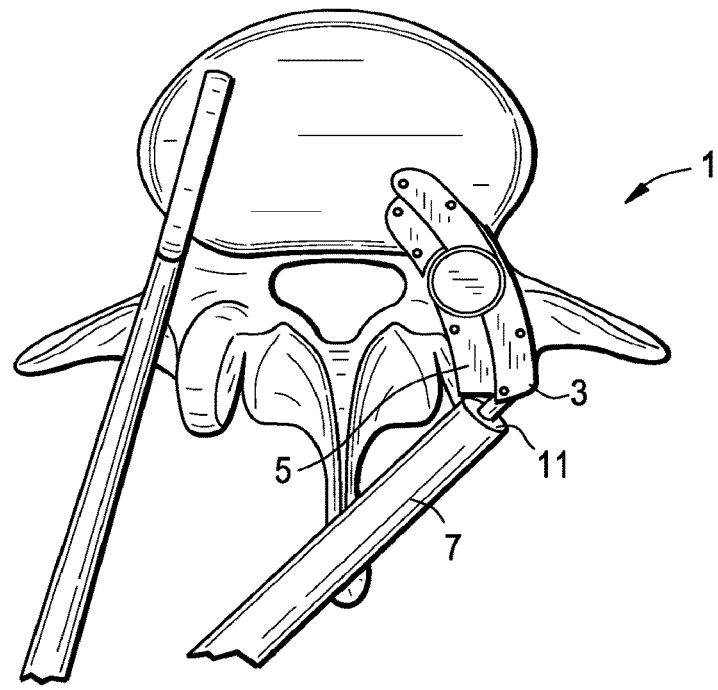
FIG. 1 discloses inserting a first motion disc/inserter assembly into the disc space, wherein the motion disc is in a collapsed condition.
Figure 2:
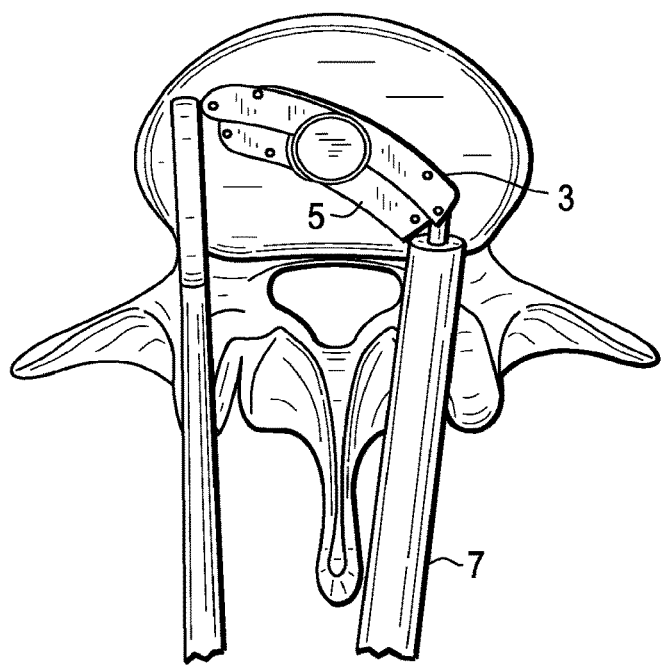
FIG. 2 discloses advancing the motion disc of FIG. 1 further into the disc space to rotate the motion disc.

Now referring to FIGS. 1-4, there is provided a method of inserting a motion disc having a first and second legs connected by a pivot, each leg having an endportion, the method comprising the steps of:
  a) providing the motion disc 1 in a collapsed position wherein the first 3 and second 5 leg endportions are close together,
  b) providing a motion disc inserter 7 comprising a handle having a longitudinal axis and a first end 11 having first 13 and second holders, the deployer being axially moveable along the axis of the handle,
  c) attaching the first endportion of the motion disc to the first holder,
  d) attaching the second endportion of the motion disc to the deployer,
  e) inserting the motion disc into the disc space in the collapsed condition, and
  f) axially moving the deployer to move the second leg and to expand the motion disc into an open condition.

In particular, and now referring to FIG. 1, the motion disc inserter secures the proximal portion of the motion disc implant for insertion into the disc space by grasping the top and bottom aspects of the proximal portion of the intradiscal device. Now referring to FIG. 2, the implant is inserted into its desired location in the disc space.

Figure 3:
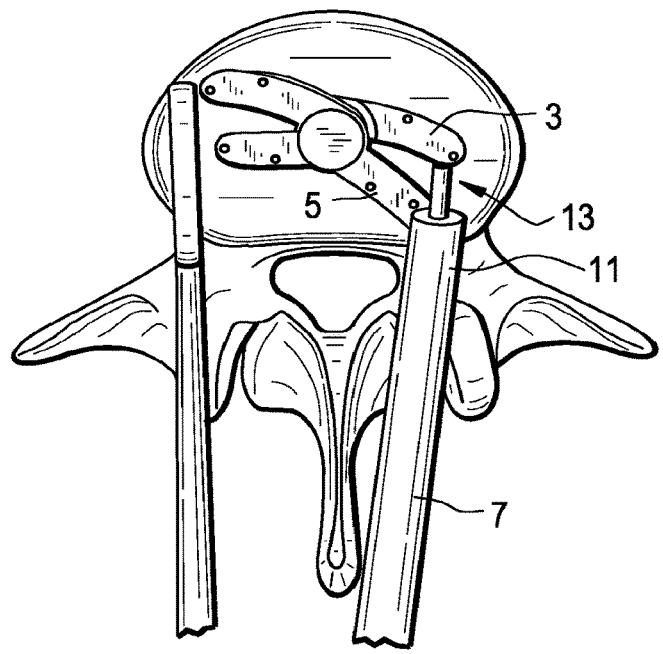
FIG. 3 discloses the initial actuation of the deployer to expand the motion disc to a partially expanded condition.

Now referring to FIG. 3, with the implant in its desired location, the deployment component of the inserter is activated to expand or adjust the implant shape for improved vertebra body contact and balanced load transfer. In particular, the expansion component of the inserter is activated to move the deployer axially and thereby pivot one of the legs of the implant shape. This produces expansion of the implant, improved vertebra body contact and a more balanced load transfer. Means for the axial movement of the deployer (and thereby the second leg) include: a) a rod that is slideably movable within a tube, b) a threaded rod that is threadably movable within a threaded tube, and c) a notched rod that is capable of ratcheted actuation.

Figure 4:
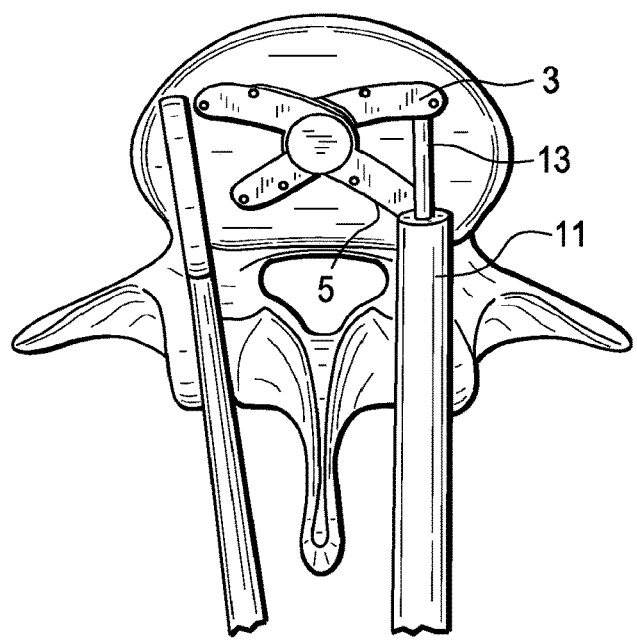
FIG. 4 discloses the complete actuation of the deployer to expand the motion disc to a final expanded condition.

FIG. 4 shows the motion disc in its expanded condition after it has been expanded by activation of the inserter.

The extent to which the deployer can be axially moved can be monitored via depth markings. In some embodiments, the depth markings are placed on the deployer. In some embodiments, the depth markings are placed on the insertion handle.

Although the inserter/deployer is shown in FIGS. 1-4 as being utilized in a posterior approach, it can be also used for other angles of approach, including lateral, anterior, and postero/lateral approaches.

The implant used in conjunction with the first embodiment can be of varying shape and configurations. Typically, it has at least one pivoting leg. In some embodiments, it has a pair of pivoting legs. An "X shaped" implant is shown in FIG. 1-4. The X-shape can have multiple layers wherein inferior and superior layers are held or deployed individually or simultaneously. Other disc implant geometries can utilizes the inserter holder/deployer of the first embodiment to insert an implant and change the footprint via disclosed the deployment means. An example of an alternate geometry is a "T"-, "Y"- or "H"-shaped implant.

In some embodiments, the handle portion of the present invention comprises a tube within which the deployer is contained. In some embodiments, the first holder is fixedly attached to the distal end portion of the tube. In other embodiments, the handle portion of the present invention comprises a solid rod, and the holders are attached to the outer surface of the rod.

The insertion track of the second embodiment of the present invention is curvilinear and has a blade, semi-tubular or tubular construction, thereby allowing negotiation of bony or soft tissues without damaging those tissues. This track provides a fixed route for insertion and rotation of the motion disc. In some embodiments, it has a substantially linear proximal portion and a curved distal portion. In some embodiments, the linear proximal portion is tubular. In some embodiments, the curved distal portion can also be tubular. However, in other embodiments, the curved distal portion can comprise upper and lower rails that mate with the upper and lower aspects of the motion disc. The insertion track also allows insertion of the motion disc via a trajectory more comparable to that of the inner wall of the annulus fibrosus, as compared to "line of site" linear insertion techniques. This compatible trajectory has the advantage of intruding upon less of the annulus fibrosus during device insertion. In use, the track is inserted into the disc space prior to insertion of the motion disc. Doing so creates an annular shield around the implant so that the implant can be safely inserted into the disc space. The curved feature of the insertion track also creates a guide for turning the device during device placement. It may also provide a method of changing the device footprint by virtue of a guiding pusher for expansion of shape.

Figure 5:
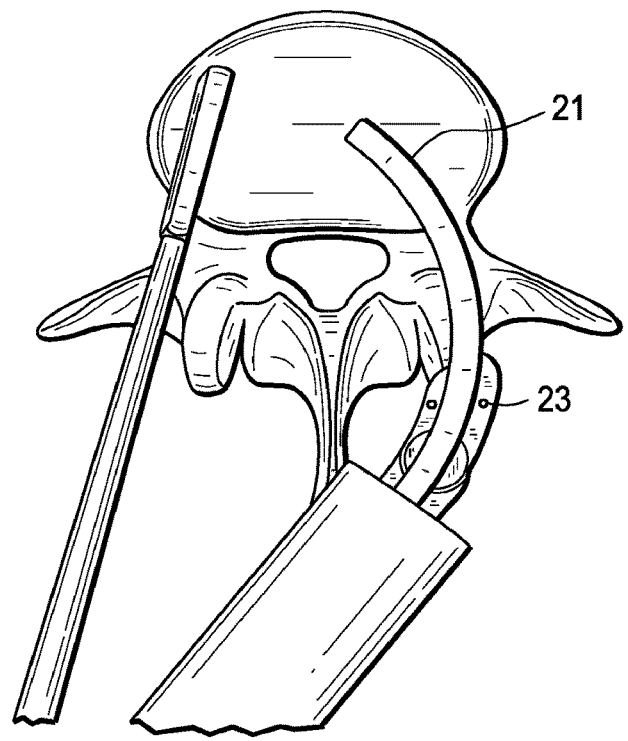
FIG. 5 discloses advancing a motion disc up a linear proximal portion of a second motion inserter, wherein the motion disc is in a collapsed condition.

Now referring to FIG. 5, there is provided an insertion track 21 of the present invention following its insertion into the disc space along the annular inner wall.

Figure 6:
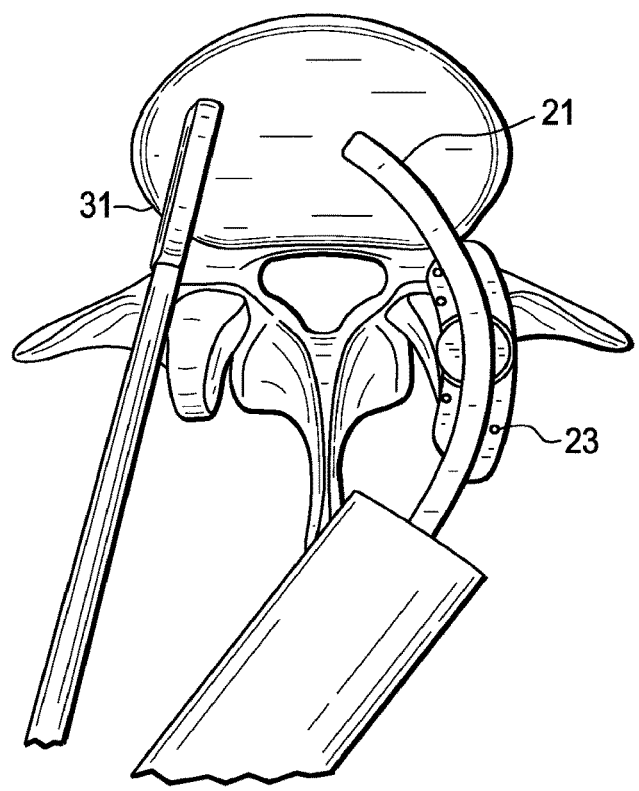
FIG. 6 discloses further advancing the motion disc of FIG. 5 through a curved intermediate portion of the inserter to rotate the motion disc.
Figure 7:
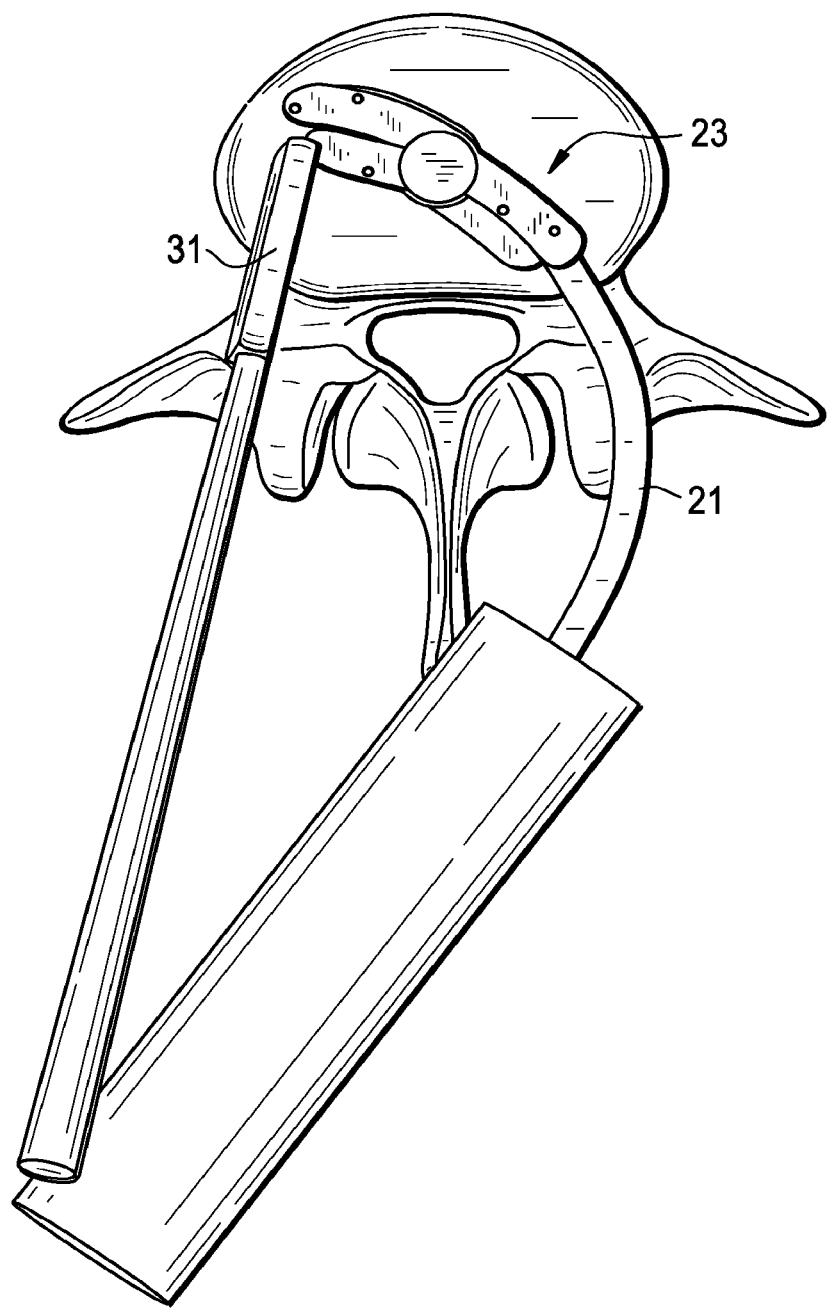
FIG. 7 discloses further advancing the motion disc of FIG. 6 through a curved distal portion of the inserter to insert the motion disc into the disc space.

Now referring to FIG. 6, a motion disc implant 23 is shown advancing along this insertion track to enter the disc space. Now referring to FIG. 7, the implant is advanced along the track until its final desired central placement is obtained. The placement depth can be limited by a positive stop(s) along the insertion track (proximal tip stop (not shown)). The depth to which the implant is inserted into the disc space can be monitored via depth markings provided on the track and referencing off an adjacent vertebral body.

Several methods of advancing the device along the insertion track can be carried out in accordance with the present invention. These methods include using a pusher instrument that holds and pushes the proximal end of the implant to advance it distally along the track. Another possible method may use a puller comprising a cable wrapped around a pulley located at the distal tip of the track, wherein one free end of the cable is connected to the implant and the other free end extends out of the proximal tubular portion of the insertion track. In this case, providing a tensile or pull force on the cable moves the device distally along the track and into the disc space.

Figure 8:
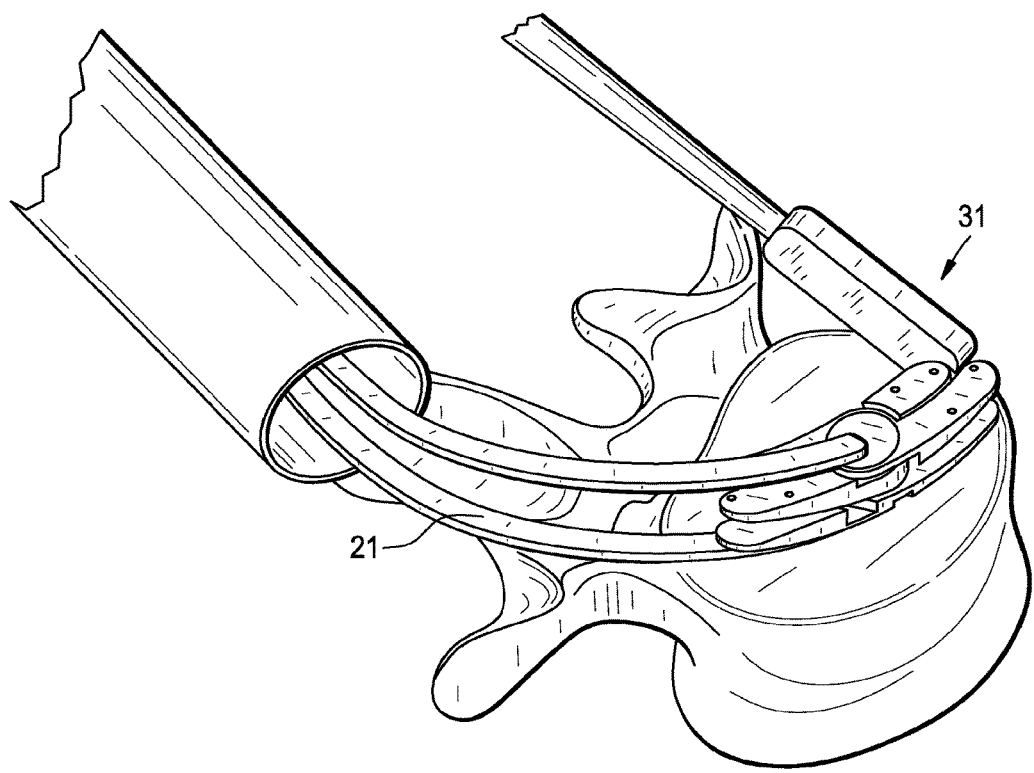
FIG. 8 discloses the final placement of the motion disc of the FIG. 7 in the disc space.

Various methods of deployment can be used to change the device footprint once the motion disc is placed within the disc space. In one embodiment, the method includes temporarily attaching interconnecting features that connect the insertion track to the implant, and withdrawing the insertion track from the disc space, thereby changing the footprint of the implant via the insertion track extraction forces. In a second embodiment, and now referring to FIG. 8, the method includes placing on the contra-lateral side of the disc space an instrument to create an advancement stop. Instrument 31 has a puller mechanism, activating the puller mechanism and pulling or pushing the motion disc into position In alternate embodiments, the contralateral puller or pusher mechanism may be actuated to change the footprint configuration of the motion disc.

In some embodiments, the insertion track can be directly connected to the implant, which provides the advantage of controlled trajectory and final position. In other embodiments, the insertion track can be connected to a holder/spacer that is attached to the implant and the insertion track, which provides the advantage of determining the angle of approach and entry for the puller/pusher mechanism.

The implant used in conjunction with the second embodiment can be of varying shape and configurations. Typically, it has at least one pivoting leg. In some embodiments, it has a pair of pivoting legs. An X-shaped implant is shown in FIGS. 5-8. The X-shape can have multiple layers, wherein various inferior and superior layers are held and/or deployed individually or simultaneously. Other disc implant geometries can exploit the insertion track to insert an implant and change the footprint via disclosed deployment means. In some embodiments, the alternate implant geometry comprises a "T"-, "Y"- or "H"-shaped implant.

FIGS. 9-12 disclose the insertion and actuation of an H-type motion disc using the insertion track inserter of the present invention. This motion disc has a central body 51 having first 53 and second 55 endportions, wherein a first leg 57 is pivotally attached to the first endportion at a first pivot, and wherein a second leg 61 is pivotally attached to the second endportion at a second pivot. Upon expansion, each of the legs of this device pivots to an orientation perpendicular to the longitudinal axis of the central body, and the device takes on an "H" shape.

Figure 9:
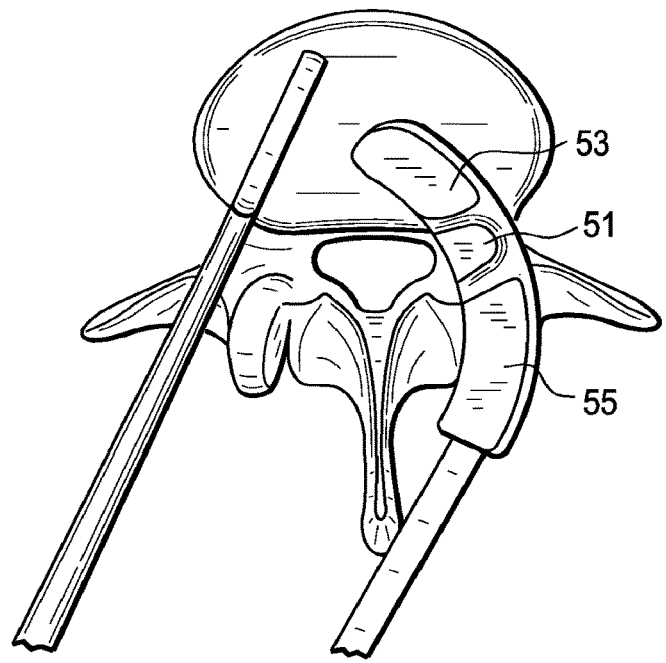
FIG. 9 discloses advancing an H-type motion disc up a linear proximal portion of a second motion inserter, wherein the motion disc is in a collapsed condition.
Figure 10:
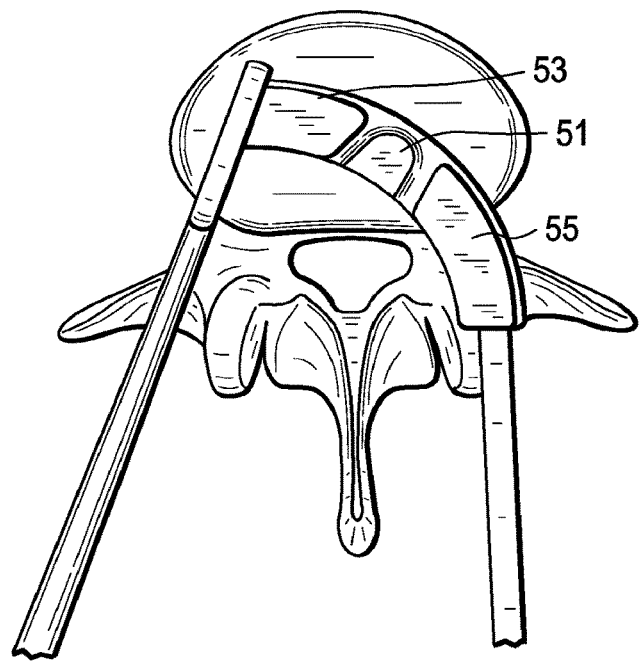
FIG. 10 discloses further advancing the motion disc of FIG. 9 through a curved distal portion of the inserter to rotate the motion disc and insert the motion disc into the disc space.
Figure 11:
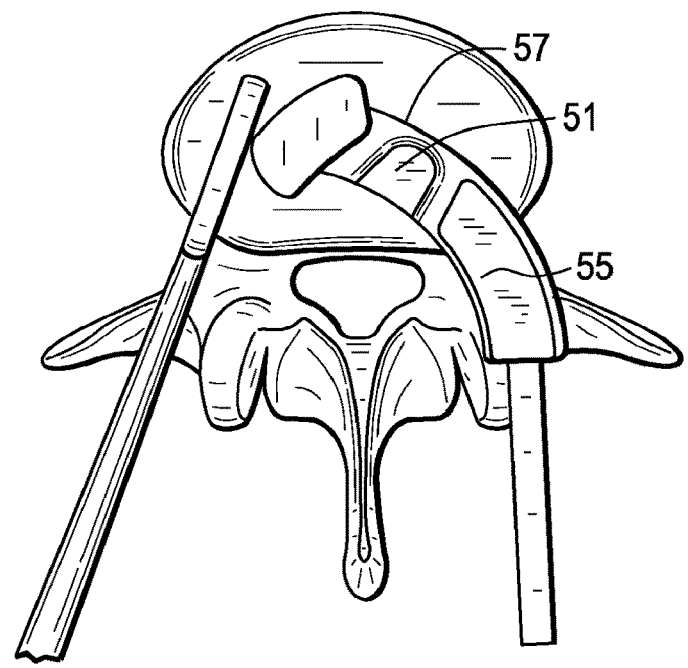
FIG. 11 discloses the initial actuation of the motion disc of FIG. 10 to expand a first leg of the motion disc.
Figure 12:
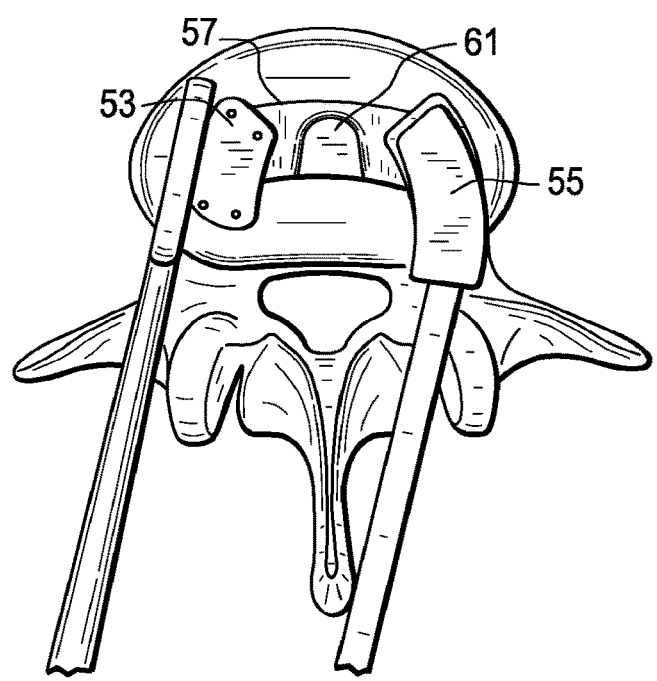
FIG. 12 discloses the final actuation of the motion disc of FIG. 11 to expand a second leg of the motion disc.

Now referring to FIG. 9, an H-type motion disc in a collapsed condition is advanced up a linear portion of the insertion track inserter. Now referring to FIG. 10, the H-type motion disc is further advanced through a curved portion of the insertion track inserter to rotate the motion disc and insert the motion disc into the disc space. Now referring to FIG. 11, initial actuation of the motion disc causes the pivoting of first leg of the motion disc and initial expansion of the motion disc. Now referring to FIG. 12, final actuation of the motion disc causes pivoting of the second leg of the motion disc and complete expansion of the motion disc.

Irrespective of the embodiment selected, if desired, an optional guide 101 (shown in FIG. 8) can be utilized during insertion and deployment to assist the surgeon in any one of disc space distraction, implant positioning, implant expansion, and/or verifying implant placement. This guide is typically placed on a contralateral side of the disc space. When the guide is used as a distractor, it typically has a transverse cross-section having a height and a width, wherein the width is greater than the height. The distractor is inserted into the disc space contralaterally so that its height dimension bears against the endplates. Prior to insertion of the motion disc, the distractor is rotated 90 degrees so that its width dimension now bears against the endplates, thereby increasing the height of the disc space.

Irrespective of the embodiment selected, in some embodiments, the inserter/deployer (as shown in FIGS. 1-4) or the insertion track (as shown in FIGS. 5-8) is used in a freehand manner. However, in other embodiments, the inserter/insertion track further comprises a docking means to dock onto or reference off nearby stable landmarks such as a vertebral body edge or a pedicle screw. Docking off of these locations provides for enhanced surgical stability and control.

Irrespective of the embodiment selected, intraoperative imaging techniques (including fluoroscopy) can be used to assist in or verify placement and deployment of the inserter and/or motion disc. Although the primary surgical approach shown is posterior or posterior/lateral, other approaches can be utilized.

Although the inserter/deployer and insertion track inserters are shown as being utilized posteriorly, they can be also used for other angles of approach including lateral, anterior, and posterior/lateral approaches.

We claim:

1. A method of implanting an intervertebral implant comprising the steps of:
   inserting the intervertebral implant into an intervertebral disc space;
   pivotally moving a first leg with respect to a body between a first orientation whereby a central leg axis of the first leg is angularly offset from a longitudinal axis of the body, and a second orientation whereby the central leg axis extends substantially in a common direction as the longitudinal axis,
   wherein the first leg has a first external surface that is concave along an entirety of the first external surface, a second external surface that is opposite the first external surface and is convex along an entirety of the second external surface, and the second external surface is spaced from the first external surface along a central leg axis of the first leg, and in the second orientation the leg defines a distance from the first external surface to the second external surface along the central leg axis, the distance less than a width of the body measured along a direction perpendicular to the longitudinal axis.

2. The method as recited in claim 1, wherein the body has a proximal endportion and a distal endportion, and the moving step comprises pivotally moving the first leg about to the proximal endportion of the body.

3. The method as recited in claim 2, wherein the first leg is pivotally coupled to the body.

4. The method of claim 2, wherein the body has an intermediate portion comprising a convex sidewall and a concave sidewall, wherein the convex sidewall is substantially parallel to the concave sidewall.

5. The method as recited in claim 1, wherein the first leg is pivotally coupled to the body.

6. The method of claim 1, wherein the longitudinal axis of the body is a curvilinear longitudinal axis.

7. The method of claim 1, comprising the step of contacting an adjacent vertebral body with the first leg.

8. The method of claim 1, wherein the first leg defines an upper surface of the implant.

9. The method of claim 1, wherein the first leg defines a leg width along the direction perpendicular to the longitudinal axis, and the leg width is less than the body width when the first leg is in the first orientation.

10. The method of claim 1, wherein the central leg axis is substantially perpendicular to the longitudinal axis when the first leg is in the first orientation.

11. A method of implanting an intervertebral implant that includes a body having endplates spaced from each other along a transverse direction, a longitudinal axis and proximal and distal endportions spaced from each other along the longitudinal axis, wherein the body has a body width along a direction perpendicular to both the longitudinal axis and the transverse direction, the method comprising the steps of:
inserting the intervertebral implant into an intervertebral disc space;
pivotally moving a first leg about a proximal endportion of the body between a first orientation whereby the first leg is substantially inline with the longitudinal axis of the body to provide a first implant footprint, to a second orientation whereby the first leg is angularly offset with respect to the longitudinal axis of the body so as to produce a second implant footprint that is different than the first implant footprint,
wherein when the leg is in the first orientation, 1) the first leg has a leg width along the direction perpendicular to both the longitudinal axis and the transverse direction, and 2) the leg width along an entirety of the first leg is less than the body width along an entirety of the body.

12. The method of claim 11, wherein the longitudinal axis of the body is a curvilinear longitudinal axis.

13. The method of claim 11, further comprising the step of contacting the first leg with an adjacent vertebral body in an intervertebral disc space.

14. The method of claim 11, wherein the distal endportion is offset from the proximal endportion in a distal direction, and the pivotally moving step comprises causing the concave surface to face the distal direction when the first leg is in the second orientation.

15. The method of claim 11, wherein the first leg defines a first leg distance from the concave surface to the convex surface, and the first leg distance is less than the body width.

16. The method of claim 11, wherein the proximal endportion is spaced from the distal endportion in a proximal direction, and the pivotally moving step comprises causing a proximal-most surface of the first leg to be offset from the body in the proximal direction when the first leg is in the second orientation.

17. The intervertebral implant of claim 16, wherein the pivotally moving step comprises causing the convex surface to be spaced from the concave surface in the proximal direction when the first leg is in the second orientation.

18. The method of claim 11, further comprising the step of attaching an inserter to the first leg of the intervertebral implant.

19. The method of claim 11, wherein the first leg is pivotally attached to the proximal end portion.

20. The method of claim 11, wherein the first leg having a first external surface that is concave along an entirety of its length, and a second external surface that is opposite the first external surface and convex along an entirety of its length.

\* \* \* \* \*